(12) United States Patent
Sungkorn et al.

(10) Patent No.: US 10,229,344 B2
(45) Date of Patent: Mar. 12, 2019

(54) REPRESENTATIVE ELEMENTARY VOLUME DETERMINATION VIA CLUSTERING-BASED STATISTICS

(71) Applicant: Ingrain, Inc., Houston, TX (US)

(72) Inventors: Radompon Sungkorn, Houston, TX (US); Jonas Toelke, Houston, TX (US); Yaoming Mu, Houston, TX (US); Carl Sisk, Indianapolis, IN (US); Abraham Grader, Houston, TX (US); Naum Derzhi, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/300,756

(22) PCT Filed: Mar. 30, 2015

(86) PCT No.: PCT/US2015/023419
§ 371 (c)(1),
(2) Date: Sep. 29, 2016

(87) PCT Pub. No.: WO2015/153505
PCT Pub. Date: Oct. 8, 2015

(65) Prior Publication Data
US 2017/0018096 A1    Jan. 19, 2017

Related U.S. Application Data

(60) Provisional application No. 61/972,990, filed on Mar. 31, 2014.

(51) Int. Cl.
*G06K 9/62* (2006.01)
*G01N 33/24* (2006.01)
(Continued)

(52) U.S. Cl.
CPC .......... *G06K 9/6218* (2013.01); *G01N 33/24* (2013.01); *G06T 7/0004* (2013.01); *G06T 7/62* (2017.01);
(Continued)

(58) Field of Classification Search
CPC .................. G06T 7/0004; G06T 7/62; G06T 2207/10056; G06T 2207/20021;
(Continued)

(56) References Cited

U.S. PATENT DOCUMENTS 8,504,491 B2    8/2013  Thiesson et al.
2009/0259446 A1  10/2009  Zhang et al.
(Continued)

FOREIGN PATENT DOCUMENTS

EP    1173816     1/2002
WO    0065481    11/2000
(Continued)

OTHER PUBLICATIONS

Thomas, M. et al. "Representative Volume Element of Anisotropic Unidirectional Carbon-Epoxy Composite with High-Fibre Volume Fraction," Composites Science and Technology, vol. 68, No. 15-16, XP025670373, Dec. 1, 2008, p. 3184-3192.
(Continued)

*Primary Examiner* — Ping Y Hsieh
(74) *Attorney, Agent, or Firm* — Chamberlain Hrdlicka

(57) ABSTRACT

An example method includes acquiring two-dimensional (2D) or three-dimensional (3D) digital images of a rock sample. The method also includes iteratively analyzing property measurements collected throughout the digital images using different subsample sizes to identify a property distribution convergence as a function of subsample size. The method also includes selecting a smallest subsample size associated with the property distribution convergence as
(Continued)

a representative elementary area or volume for the rock sample.

18 Claims, 6 Drawing Sheets

(51) Int. Cl.
  *G06T 7/00* (2017.01)
  *G06T 7/62* (2017.01)
(52) U.S. Cl.
  CPC .............. *G06T 2207/10004* (2013.01); *G06T 2207/10012* (2013.01); *G06T 2207/10056* (2013.01); *G06T 2207/20021* (2013.01); *G06T 2207/30181* (2013.01)
(58) Field of Classification Search
  CPC ........... G06T 2207/10012; G06T 2207/30181; G06K 9/6218; G01N 33/24
  See application file for complete search history.

(56) References Cited

U.S. PATENT DOCUMENTS

| | | | | |
|---|---|---|---|---|
| 2010/0228486 | A1* | 9/2010 | Wu | G01V 1/30 702/17 |
| 2012/0283989 | A1* | 11/2012 | Hirohata | H04L 29/00 702/180 |
| 2013/0262028 | A1* | 10/2013 | De Prisco | G01N 33/24 702/156 |
| 2013/0338976 | A1* | 12/2013 | De Prisco | G06T 7/41 703/2 |
| 2014/0044315 | A1 | 2/2014 | Derzhi et al. | |

FOREIGN PATENT DOCUMENTS

| | | |
|---|---|---|
| WO | 2012118867 A2 | 7/2012 |
| WO | 2013188239 A2 | 12/2013 |
| WO | 2015/153505 | 10/2015 |
| WO | 2015153506 | 10/2015 |

OTHER PUBLICATIONS

Wang, Hai Xian et al. "Estimation for the Number of Components in a Mixture Model Using Stepwise Split-and-Merge EM Algorithm," Pattern Recognition Letters, Elsevier, Amsterdam, NL, vol. 25, No. 16, XP004619671, Dec. 1, 2004, p. 1799-1809.
Konstantinos Blekas, "Split-Merge Incremental Learning (SMILE) of Mixture Models," Artificial Neural Networks—Icann, Springer Berlin Heidelberg, Berlin, XP019069466, Sep. 9, 2007, p. 291-300.
"AU Patent Examination Report", dated Mar. 6, 2017, Appl No. 2015241029, "Reprentative Elementary Volume Determination via Clustering-based Statistics," Filed Mar. 30, 2015, 3 pgs.
"PCT International Search Report and Written Opinion", dated Jul. 7, 2015, Appl No. PCT/US2015/023419, "Reprentative Elementary Volume Determination via Clustering-based Statistics, " filed Mar. 30, 2015, 11 pgs.
Bishop, Chapter 9: "Mixture Models and EM," Pattern Recognition and Machine Learning, Springer Science +Business Media LLC, eds. Jordan et al., Singapore, 2006: pp. 423-459.
Donstanza-Robinson et al., "Representative elementary volume estimation for porosity, moisture saturation, and air-water interfacial areas in unsaturated porous media: Data quality implications," Water Resources Research, Jul. 2011, vol. 47(W07513): pp. 1-12.
Do et al., "What is the expectation maximization algorithm?," Nature Biotechnology, Aug. 2008, vol. 26(8): pp. 897-899.
Ma et al., "A Dynamic Merge-or-Split Learning Algorithm on Gaussian Mixture for Automated Model Selection*," Ideal, 2005: pp. 203-210.
Ueda et al., "SMEM Algorithm for Mixture Models," Journal of Neural Computation, Sep. 2000, vol. 12(9): pp. 2109-2128.
Zhang et al., "EM algorithms for Gaussian mixtures with split-and-merge operation," Pattern Recognition 36, 2003: pp. 1973-1983.

* cited by examiner

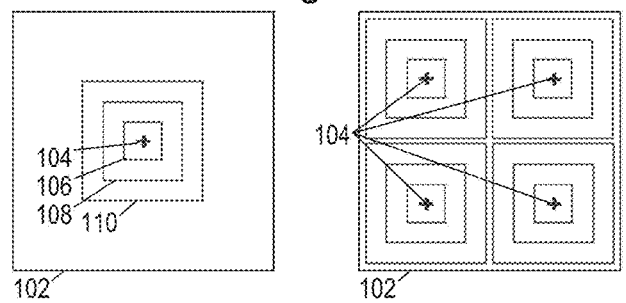
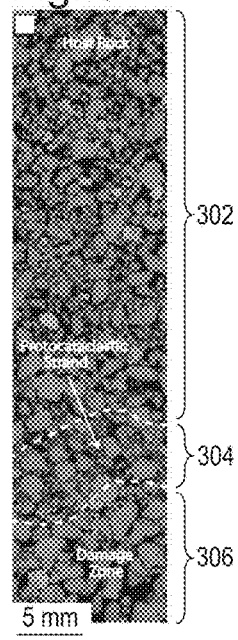
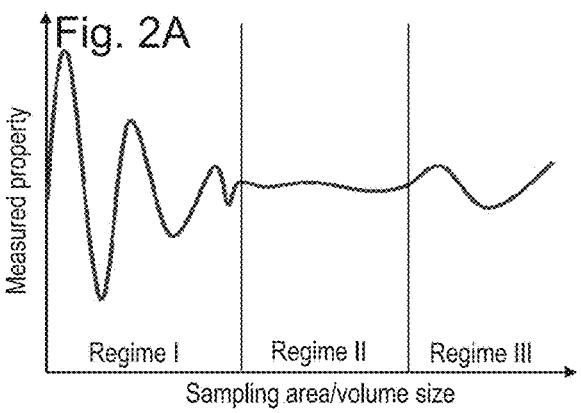
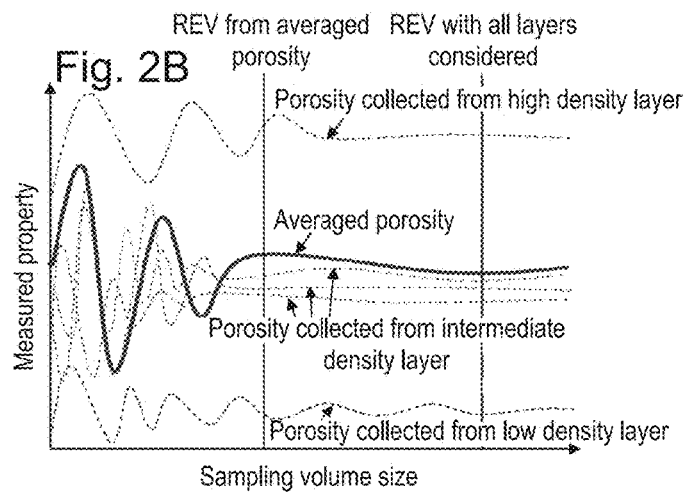

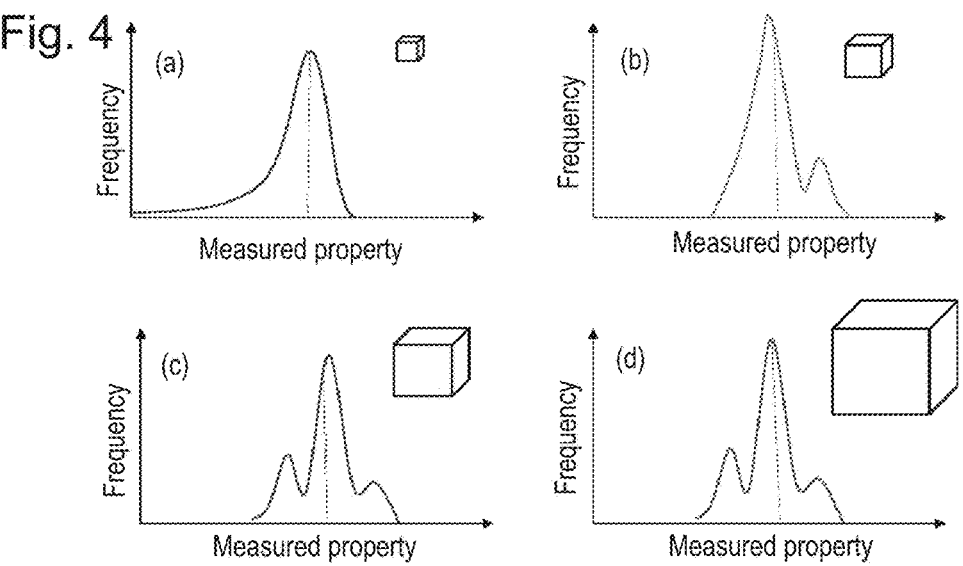

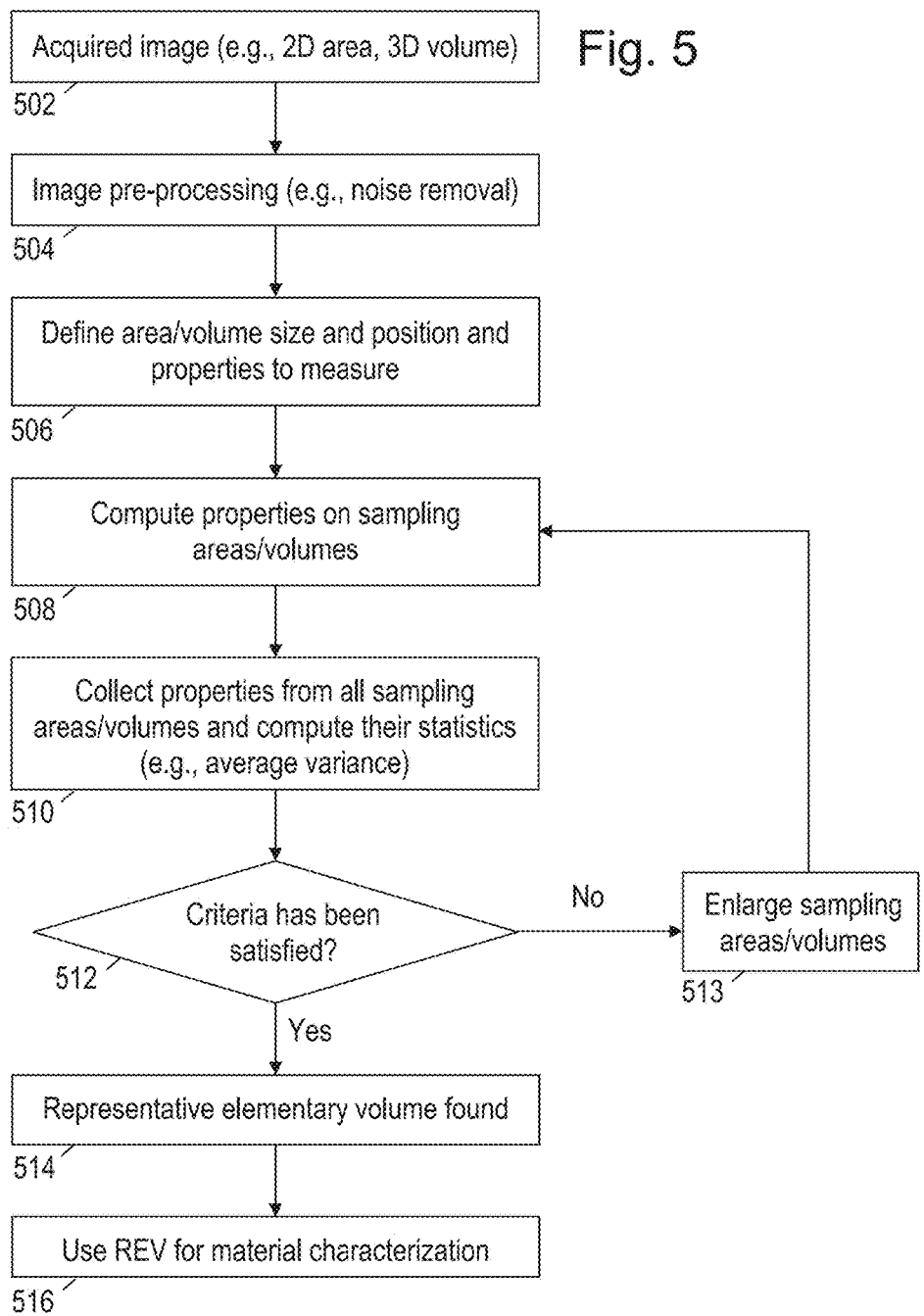

REPRESENTATIVE ELEMENTARY VOLUME DETERMINATION VIA CLUSTERING-BASED STATISTICS

CROSS-REFERENCE TO RELATED APPLICATIONS

The present application claims priority to U.S. Patent Application 61/972,990 titled "Representative Elementary Volume Determination via Clustering-Based Statistics", filed Mar. 31, 2014 by inventors Radompon Sungkorn, Jonas Toelke, Yaoming Mu, Carl Sisk, Avrami Grader, and Naum Derzhi, which is incorporated by reference in its entirety.

BACKGROUND

Advanced imaging technologies, such as microscopy and spectroscopy, have often been employed by scientists and engineers to gain insights into materials of interest. Such technologies provide a two (or higher) dimensional magnified image of the material (or at least a part thereof). Analysis techniques may then be applied on the acquired image to visualize the internal structure and/or to characterize the material. Depending on the analysis, a number of characteristic properties are measured and quantified, such as structure, type and number of distinct phases, phase morphology, and phase chemistry.

Regardless of the characteristic properties being measured, it is recognized that a majority of natural and man-made materials possess a high degree of heterogeneity, often as the result of varying voids and grain sizes. Such heterogeneity often makes it challenging to find a suitable sample volume that, for the purposes of engineering analysis, may be regarded as representative of the material body as a whole. Typically, the smallest such volume (or, in the case of a two dimensional image, the smallest such area) is called the representative elementary volume ("REV").

There are a number of existing REV determination procedures, at least one of which performs adequately for relatively homogenous materials. See, e.g., Costanza-Robinson, et al. "REV estimation for porosity, moisture saturation, and air-water interfacial areas in unsaturated porous media: Data quality implications", Water Resources Research, v47, W07513, 2011. Nevertheless, existing methods may suffer from a number of shortcomings, including overestimation, overly-generous search region requirements, overly-restrictive subsample positioning requirements, and a general inability to cope with relatively heterogeneous materials.

SUMMARY

Accordingly, there is disclosed herein systems and methods for performing representative elementary volume ("REV") determination via clustering-based statistics. The disclosed systems and methods extend the REV concept so as to enable the number and type of REV properties to be chosen in light of the material, thereby producing a better representation of the material that includes the REV size and further includes the number and location of distinctive regions in the material.

The disclosed systems and methods may benefit from the use of a novel clustering method that is also disclosed herein for this and other purposes as well. The novel clustering method operates on complex and/or large data sets to identify the number of clusters and their associated parameters. An iterative split-and-merge process is employed to split clusters having a low likelihood of representing the data set, before merging those clusters that a data set-based criterion indicates should be merged.

BRIEF DRAWING DESCRIPTION

FIG. 1 shows an illustrative relationship of a sample to multiple subsamples.

FIGS. 2A-2B shown an illustrative property dependence on subsample size.

FIG. 3 is an image of an illustrative heterogeneous sample.

FIGS. 4A-D shows an illustrative subsample size dependence of a property distribution.

FIG. 5 is a flowchart of an illustrative REV determination method.

Figure 7A:
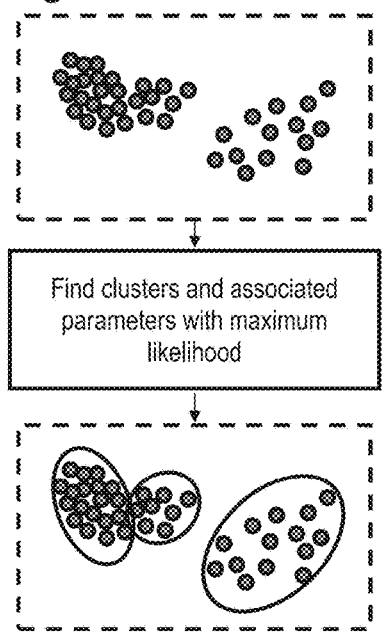
Figure 7B:
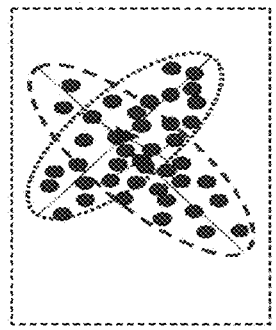
Figure 7C:
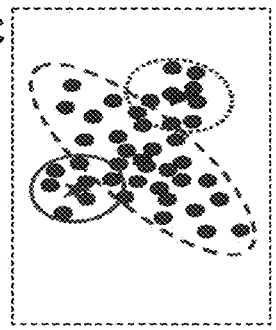

FIGS. 7A-7C demonstrate an illustrative clustering process.

Figure 8:
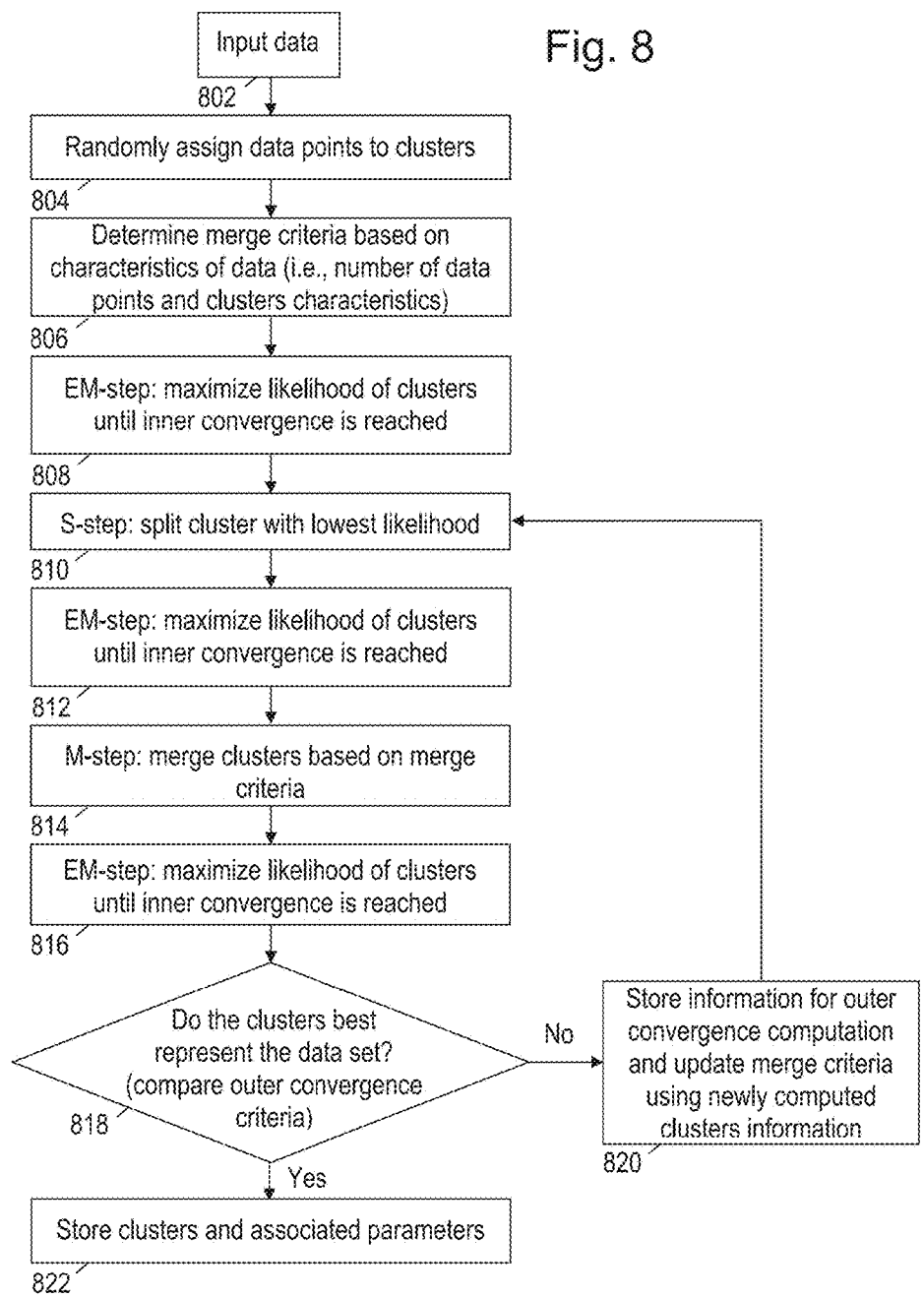

FIG. 8 is a flowchart of an illustrative clustering method.

Figure 9:
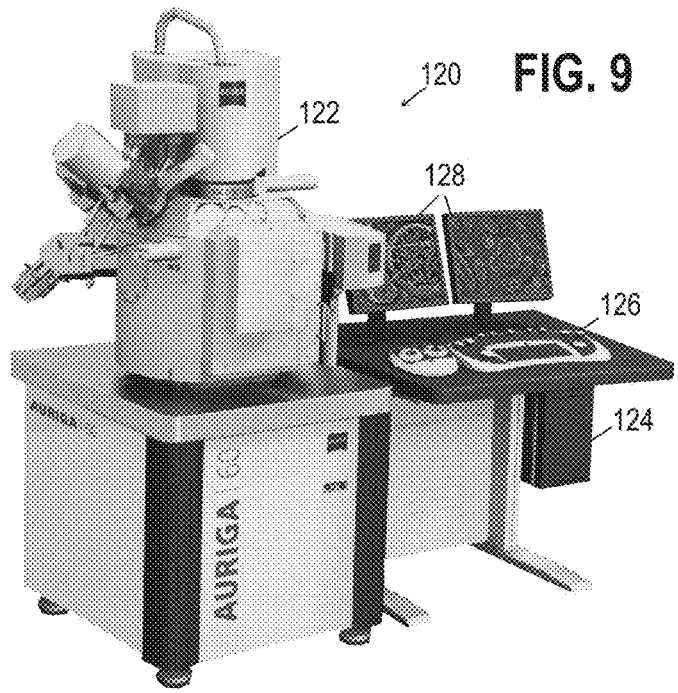

FIG. 9 is an illustrative imaging system.

Figure 10:
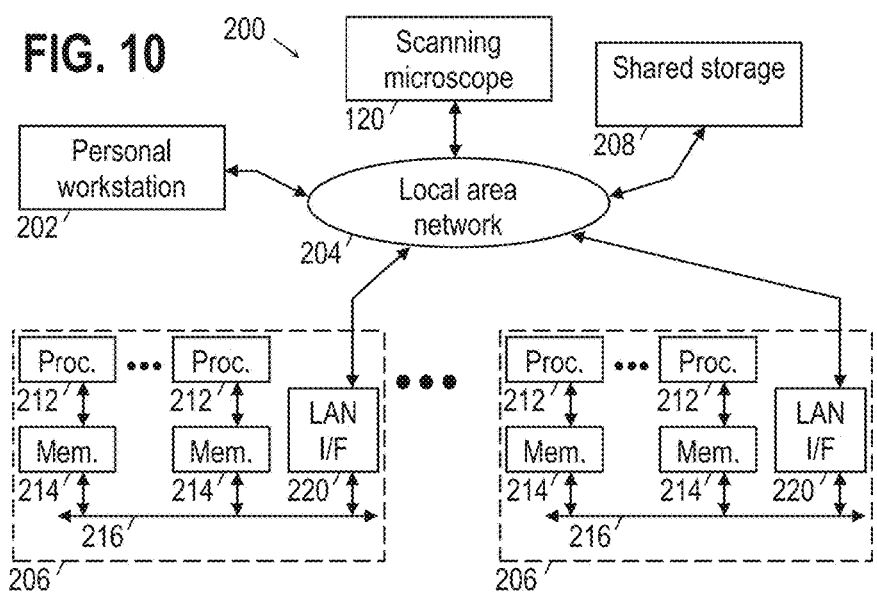

FIG. 10 is an illustrative computer system that may be used to implement the disclosed methods.

DETAILED DESCRIPTION

We begin with a reconsideration of the conventional approach to determining the representative elementary volume ("REV"). For convenience, the drawings employ two-dimensional images, but the described principles are applicable to three dimensional volumes as well. FIG. 1 shows an image 102 of the sample (duplicated to better illustrate the usage of potentially overlapping subsamples), in which a number of subsample positions 104 have been randomly or systematically chosen. The search for the REV of the sample employs the use of gradually increasing subsample sizes, shown in FIG. 1 as increasing perimeters 104, 106, 108, and 110. A selected property is measured for each of the subsamples and the measurements are combined and plotted as a function of the subsample size (usually, though not necessarily, expressed in terms of the length of one edge).

FIG. 2A shows an example of such a plot for a relatively homogeneous material, where the average subsample porosity (ratio of void area to total area) is plotted as a function of subsample side length. The plot can be divided into three regimes I, II, III, based on the volatility of the curve's dependence on subsample size. As the subsample size gradually increases from near zero (regime I), the curve exhibits a large but gradually decreasing volatility until it stabilizes and enters a range having little dependence on sample size (regime II). In many cases, if the sample size continues to increase, larger scale heterogeneities begin re-introducing volatility to the curve (regime III). Traditionally, the boundary between regime I and II is chosen as the REV size. Various decisions made during this analysis (shape and number of subsamples, subsample position selection, measured subsample property, statistic used to combine subsample measurements, threshold for determining stability) can affect the resulting value for the REV, but this approach is generally representative.

However, as shown by the example of FIG. 3, many sampled materials are relatively heterogeneous. In this image, dark areas represent pore space and lighter areas represent grain. A porosity-based characterization indicates that this material includes three distinct layers: a host rock layer 302, a proto-cataclastic layer 304, and a damage zone layer 306, each having different porosities. (The damage zone layer 306 has the highest porosity, the host rock layer 302 has smaller grains with reduced porosity, and the intermediate layer 304 has a mixture of fine and coarse grains that yields the lowest porosity.) The REV determination procedure outlined in the discussion of FIGS. 1 and 2 copes poorly when applied to heterogeneous materials. If all subsample positions are confined to a single layer, the remainder of the sample is not properly characterized, whereas the inclusion of multiple layers fails to reflect the true heterogeneity of the sample.

As an example, assume for the ease of discussion that there are five subsample positions, with one in the host rock layer 302, three in the proto-cataclastic layer 304, and one in the damage zone 306. The dependence of the five subsamble porosities on subsample size are shown as broken lines in FIG. 2B. Considered separately, the low porosity layer curve results in the a REV size represented by the rightmost vertical line. However, the average curve (shown as a solid line) results in a REV size represented by the first vertical line. Note the large discrepancy between the two.

Consequently, it is proposed that the property vs. size stability criterion be dropped in favor of a property distribution vs. size criterion. FIGS. 4A-4D each show, for different subsample sizes, an illustrative histogram or probability distribution function of the property measurements obtained with different subsample sizes. It can be seen that at small subsample sizes, the property distributions change as a function of size, progressing in this example from a unimodal distribution to a bimodal distribution and trimodal distribution. However, at sufficiently large subsample sizes, the distribution remains stable and insensitive to subsample size. The minimum size at which this stabilization occurs may be treated as the REV.

The distribution stability criterion may be expressed in various forms. At one extreme, the distribution can be characterized solely in terms of its mean, which corresponds to the subsample averages plotted in FIGS. 2A-2B, but this extreme suffers from the same shortcomings outlined previously. Even combined use of the average and variance of the distribution is likely to yield an REV determination at the FIG. 4B level rather than the more suitable FIG. 4C level. At the opposite extreme, a full match between distribution curves at adjacent subsample sizes may be sought, using some mean-square error threshold. This "full match" appears overly rigorous, yielding unnecessarily large REV sizes.

Rather, as indicated by FIGS. 6A-6D, the property distribution may be thought of as a combination of unimodal distributions (e.g., Gaussian peaks) that each represent a different component of the overall sample, and a statistical analysis technique is applied to the distributions to determine the number, position, and variance of the unimodal distributions. The minimum size at which these parameters stabilize (to within a predetermined threshold), is that of the preferred REV. In some embodiments, the threshold used to determine that the parameters have stabilized can be adjusted up or down to expedite or fine-tune the process of determining the REV.

Figure 6:
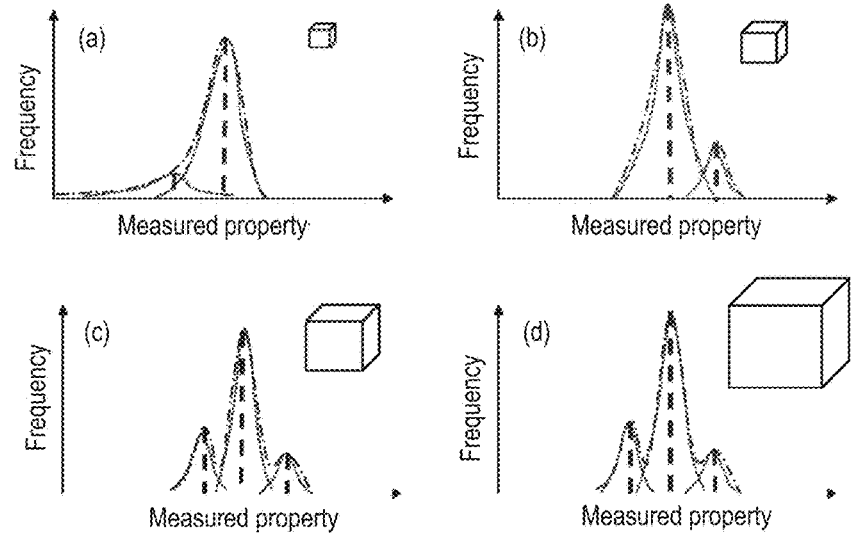
FIGS. 6A-6D show a mixed distribution model of the property distributions of FIG. 4.

Moreover, it should be noted that the unimodal distributions sought need not be limited to distributions of one variable as shown in FIG. 6. Rather, multivariate property distributions may be analyzed to determine the number, location, and variances of the constituent peaks. The increased information obtained from the use of multiple properties (e.g., porosity, pore structure including Minkowski measures of pore geometry, porous matrix composition including phase fraction, phase morphology, mineral fraction, permeability, formation factor, capillary pressure, relative permeability) is expected to yield better determinations of REV size.

A flow diagram for the method is shown in FIG. 5. In block 502, the image of the sample is captured, and in block 504 it may be pre-processed to make it more suitable for the subsequent analysis steps, e.g. by removing noise and quantifying each pixel as matrix or void or porous material. In block 506, the system sets the subsample positions and initial sizes. The number of subsamples is preferably based on population size (i.e. number of pixels/voxels), a chosen confidence level, a chosen confidence interval, and a standard of deviation. The sampling points can be placed in random or systematic fashion within the material. Alternatively, if feasible, the properties can be computed throughout the material with the chosen subsample size in an overlapping or non-overlapping manner, thereby avoiding the issue of selecting an appropriate number and location of sampling points.

Blocks 508-513 represent the search loop which iterates through a series of increasing subsample sizes. In block 508, the selected properties for the current subsamples are measured. The selected properties are determined beforehand, and their number can vary. Each of these properties will be measured and analyzed together.

In block 510, the subsample property measurements are collected and used to analyze the collective property distribution for that subsample size. Any one of a number of available statistical analysis techniques may be employed to determine the number, position, and variance of the constituent modes/groups/clusters, including the expectation-maximization method and its variations, logistic regression and variations of the Bayesian regression method. (A particularly suitable clustering method is discussed in greater detail below.) When analyzing the distribution of a single property, the analysis yields the mean, variance, and fraction (relative weighting) of each cluster. When multiple properties are analyzed, the analysis provides a mean vector, covariance matrix, and scalar fraction for each cluster.

In block 512, the results of the analysis are compared to the results determined with the previous subsample size, and if the results do not match to within some threshold, the subsample size is increased in block 513 and the loop is repeated. Once a match is found, the REV size is set to the previous subsample size in block 514, and in block 516 that REV size is used for further characterization of the sample.

As shown in FIG. 7A, the novel clustering method provided herein takes a set of points (e.g., the vectors representing the subsample property measurements) and groups them into clusters. The clusters may correspond to a sum of parameterized Gaussian distributions, where the parameters are determined to have those values that provide a maximum likelihood of representing the set of points. The novel method shares certain features of the known expectation-maximization (EM) methods that are described, for example, in the following references, which are hereby incorporated herein by reference in their entirety:

Chickering D.; Fast clustering with sparse data; patent EP1173816 B1.

Thiesson B. and Wang C.; Variational EM method for mixture modeling with component-dependent partitions; U.S. Pat. No. 8,504,491.

Wang et al.; Estimation for the number of components in a mixture model using stepwise split-and-merge EM method; Pattern Recognition Letters, 2004, vol. 25, pp. 1799-1809.

Zhang et al.; EM methods for Gaussian mixtures with split-and-merge operation; Pattern Recognition, 2003; vol. 36, pp. 1973-1983.

Ma J. and He Q.; A dynamic merge-or-split learning method on Gaussian mixture for automated model selection; in Gallagher et al. (Eds.); IDEAL 2005, LNCS 3578, 2005, pp. 203-210.

Blekas K. and Lagaris I. E.; Split-merge incremental learning (SMILE) of mixture models; Artificial Neural Networks—ICANN 2007, Lecture Notes in Computer Science vol. 4669, 2007, pp. 291-300.

Ueda et al.; SMEM method for mixture models; Neural Computation, vol. 12, 2000, pp. 2109-2128.

Do C. B. and Batzoglou S.; What is the expectation maximization method?; Nature Biotechnology, 2008, vol. 26, pp. 897-899.

Bishop C. M.; Pattern recognition and machine learning: Ch. 9 Mixture Models and EM; Springer, 2006.

Unlike existing methods, the novel method advantageously avoids solutions of the form shown in FIG. 7B, where the distribution is expressed in terms of overlapping or intersecting point subsets. Instead, as shown in FIG. 7C, the acceptable solutions exist only as clusters with minimal overlap and at least a minimum separation between means (based on the variance of the individual clusters). Moreover, this requirement is achieved without incurring an unnecessarily heavy computational burden as required by at least some of the existing EM techniques.

In addition to the set of input points, the novel method requires only a threshold value for determining convergence. Based on these inputs, the method iteratively adjusts the number of clusters and associated parameters to achieve the maximum likelihood, i.e. the likelihood that the clusters are the best representation of the data set. At the end of the method a mixture model based on the computed clusters and associated parameters is achieved with an optimum number of well-separated clusters to represent a data set and computation resources.

As shown in FIG. 8, the clustering method begins in block 802 by obtaining the set of input points. In block 804, the method generates a set of random cluster parameters (including mean, variance, and weight for each of a number of clusters determined based on the number of input points), and assigns each of the points to its most representative cluster.

In block 806, the method determines two merge criteria based on the data set. A first merge criterion is the critical merge degree. The Ma (2005) reference above establishes this criterion as $$\delta_1 = 0.004 * N^{1/2}$$

where N is the number of data points. Other critical merge criteria may also be used to set a maximum threshold for merging two different clusters.

The present method further determines a second merge criterion to enforce a minimum distance between clusters. If the centers of the clusters are below the distance threshold, they are merged. Various distance criteria may be employed for this purpose, including Euclidean distance, Mahalanobis distance, and bin size-based distance. One particularly suitable bin-size based distance measure is based on a modified Sturges' formula. The second merge criterion is:

$$\delta_2 = \acute{C} * \frac{(\emptyset_{max} - \emptyset_{min})}{2 * (\log_2 N + 1)}$$

where $\emptyset_{min}$ and $\emptyset_{max}$ represent the maximum and minimum value of the observed quantity, respectively, and $\acute{C}$ is the characteristic number of clusters. The characteristic number of clusters $\acute{C}$ may be estimated based on number and distance between the current clusters. For example, if the data set is described using a mixture of Gaussian distributions and the distance between the mean values μ of two clusters is less than either of their standard deviations σ, then one of them is omitted from the count. In contrast, if the two clusters are well separated, i.e. the distance between their mean values is greater than both of their standard deviations, they are each included in the count. Consequently, the latter case yields a larger second merge criteria. The merge criteria can be viewed as a way to minimize the number of clusters while preserving the representativeness of the computed clusters.

In block 808, the method performs an EM (optimization) step, adjusting the current cluster parameters to maximize their likelihood. This EM operation has been intensively discussed in literature, including the foregoing references. For the sake of completeness, a short discussion concerning the EM step will be repeated. Let the data set $\{x_1, x_2, x_3, \ldots, x_N\}$ be a random data points of size N from the d-dimensional data set. A d-variate mixture model for the given data set can be written as:

$$f(x|\theta) = \Sigma_{k=1}^{C} f(x|\theta_k, \pi_k)$$

where f(–) represents a selected density function with C components (i.e. C constituent clusters), $\theta_k$ is a vector of the associated parameters of the density function for the $k^{th}$ component, and $\pi_k$ is the mixing weight of the $k^{th}$ component. In the EM step, the expected log-likelihood function of the mixture model is computed from:

$$\mathcal{L}(\theta|\theta^t) = \Sigma_{n=1}^{N} \log\{\Sigma_{k=1}^{C} f(x_n|\theta_k, \pi_k)\}$$

Then, parameters that maximize $\mathcal{L}(\theta)$ are computed from:

$$\theta^{t+1} = \underset{\theta}{\arg\max} \; \mathcal{L}(\theta|\theta^t)$$

where arg max stands for the argument of the maximum. The procedure is repeated for t=1, 2, 3, . . . until a convergence based on the log-likelihood is achieved. Then the method proceeds to the next step.

In block 810, the method performs a split (S) operation on the cluster having the smallest local log-likelihood such that the overall likelihood of the mixture model is increased. The local log-likelihood may be computed from:

$$\mathcal{L}_{loc}(k) = \frac{\sum_{n=1}^{N} \log\{f(x_n | \theta_k, \pi_k)\}}{\sum_{n=1}^{N} \gamma_{n,k}}$$

where the responsibility γ of the data point n in $k^{th}$ cluster is:

$$\gamma_{n,k} = \frac{f(x_n | \theta_k, \pi_k)}{\sum_{k=1}^{C} f(x_n | \theta_k, \pi_k)}.$$

When split, the cluster with minimum log-likelihood is divided into two clusters that are offset from the local maximum. For example, in the case that the data is described using mixture model based on Gaussian distribution function with mean $\mu$, variance $\sigma^2$ and mixing weight it, a cluster with index a may be split into clusters and co as follows:

$$\pi_\beta = \pi_\omega = \frac{\pi_\alpha}{2},$$
$$\mu_\beta = \mu_\alpha + 2\sigma_\alpha,$$
$$\mu_\omega = \mu_\alpha - 2\sigma_\alpha,$$
$$\sigma_\beta^2 = \sigma_\omega^2 = \frac{\sigma_\alpha^2}{2}.$$

The S-step is followed in block 812 by another EM-step to maximize the overall log-likelihood with the new cluster included. Then, using the new parameters, a merge operation is performed in block 814. During the novel merge (M) operation implemented by the present method, a merge degree between each pair of clusters i,j is computed:

$$\Psi_{i,j} = \frac{\sum_{n=1}^{N} \gamma_{n,i} * \gamma_{n,j}}{\sum_{n=1}^{N} |\gamma_{n,i}| * \sum_{n=1}^{N} |\gamma_{n,j}|}.$$

The merge degree with minimum value is compared with the critical merge degree $\delta_1$, i.e. the first merge criterion. If the minimum merge degree is lower than $\delta_1$ this pair of clusters will be merged at the end of the M-step. In at least some embodiments, each of the cluster pairs having a merge degree below the first merge criterion are simultaneously merged.

However, before such merging is actually performed, the distance between each given cluster and the remaining clusters is evaluated. For example, for one-dimensional data with Gaussian distribution, the distance S between $i^{th}$ and $j^{th}$ cluster may be computed from the absolute difference between the means $S=|\mu_i-\mu_j|$. Cluster pairs are slated for merging whenever the distance S is less than the minimum distance $\delta_2$, i.e. the second merge criterion.

Once all of the pairs have been evaluated and one or more designated for merging, the associated parameters of the merging clusters are combined. In the case that data is described using mixture model based on Gaussian distribution function with parameters discussed above, the parameters of the new cluster $\eta$ (resulted from merge operation) may be computed as follows:

$$\pi_\eta = \sum_{p=1}^{MP} \pi_i,$$
$$\mu_\eta = \frac{\sum_{p=1}^{MP} \pi_i \mu_i}{\pi_\eta},$$
$$\sigma_\eta^2 = \frac{\sum_{p=1}^{MP} \pi_i \sigma_i^2}{\pi_\eta},$$

where the summation from p=1 to MP represents the summation of all merge pairs which satisfied the merge criteria. In block 816, the EM-step is again repeated after the M-step to maximize the overall log-likelihood.

In block 818, the method determines whether convergence has been reached by comparing the log-likelihood before the split step 810 and one after the merge step (after block 816). Convergence is indicated when the difference between the log-likelihoods is less than a pre-defined convergence criteria, and the resulting cluster parameters are displayed and/or stored for later use in block 822. For example, once convergence is reached, a cluster or property distribution index value may be assigned to each of a plurality of data points used to represent property measurements throughout 2D or 3D digital images. Further, as the data points correspond to known coordinate positions in 2D or 3D digital images, a cluster or property distribution index value may be spatially assigned to subsamples within 2D or 3D digital images. The property distribution index values may be used for subsequent analysis and characterization of the corresponding sample. For more information regarding subsequent analysis options that may benefit from property distribution index values, reference may be had to Radompon Sungkorn et al., "Digital Rock Physics-Based Trend Determination and Usage for Upscaling", PCT Application Serial Number PCT/US15/23420 and filed Mar. 30, 2015, and hereby incorporated herein by reference in its entirety. If a determination is made that convergence has not been reached (determination block 818), the log-likelihood information is stored for later reference and the merge criteria are updated (block 820) before the method returns to block 810.

The methods represented by FIG. 5 and FIG. 8 may be computer implemented using data obtained from images representing a sample. For context, FIGS. 9-10 demonstrate an illustrative context for the use of these methods. FIG. 1 shows an illustrative high-resolution focused ion beam and scanning electron microscope 120 having an observation chamber 122 in which a sample of material is placed. A computer 124 is coupled to the observation chamber instrumentation to control the measurement process. Software on the computer 124 interacts with a user via a user interface having one or more input devices 126 (such as a keyboard, mouse, joystick, light pen, touchpad, or touchscreen) and one or more output devices 128 (such as a display or printer).

For high resolution imaging, the observation chamber 122 is typically evacuated of air and other gases. A beam of electrons or ions can be rastered across the sample's surface to obtain a high resolution image. Moreover, the ion beam energy can be increased to mill away thin layers of the sample, thereby enabling sample images to be taken at multiple depths. When stacked, these images offer a three-dimensional image of the sample to be acquired. As an illustrative example of the possibilities, some systems enable such imaging of a 40×40×40 micrometer cube at a 10 nanometer resolution.

However, the system described above is only one example of the technologies available for imaging a sample. Transmission electron microscopes (TEM) and three-dimensional tomographic x-ray transmission microscopes are two other technologies that can be employed to obtain a digital model of the sample. Regardless of how the images are acquired, the foregoing disclosure applies so long as the resolution is sufficient to reveal the porosity structure of the sample.

The source of the sample, such as in the instance of a rock formation sample, is not particularly limited. For rock formation samples, for example, the sample can be sidewall cores, whole cores, drill cuttings, outcrop quarrying samples, or other sample sources which can provide suitable samples for analysis using methods according to the present disclosure.

FIG. 2 is an example of a larger system 200 within which the scanning microscope 120 can be employed. In the larger system 200, a personal workstation 202 is coupled to the scanning microscope 120 by a local area network (LAN) 204. The LAN 204 further enables intercommunication between the scanning microscope 120, personal workstation 202, one or more high performance computing platforms 206, and one or more shared storage devices 208 (such as a RAID, NAS, SAN, or the like). The high performance computing platform 206 generally employs multiple processors 212 each coupled to a local memory 214. An internal bus 216 provides high bandwidth communication between the multiple processors (via the local memories) and a network interface 220. Parallel processing software resident in the memories 214 enables the multiple processors to cooperatively break down and execute the tasks to be performed in an expedited fashion, accessing the shared storage device 208 as needed to deliver results and/or to obtain the input data and intermediate results.

Typically, a user would employ a personal workstation 202 (such as a desktop or laptop computer) to interact with the larger system 200. Software in the memory of the personal workstation 202 causes its one or more processors to interact with the user via a user interface, enabling the user to, e.g., craft and execute software for processing the images acquired by the scanning microscope. For tasks having small computational demands, the software may be executed on the personal workstation 202, whereas computationally demanding tasks may be preferentially run on the high performance computing platform 206.

When adapted for use in the illustrative systems, the methods may be modified to enable one or more of the operations to be carried out concurrently to exploit the availability of parallel processing resources. Moreover, the order of the steps may vary, with some of the steps carried out in a potentially speculative fashion. Such variations are within the scope of the claims. Fortunately the disclosed methods reduce the computational complexity to a level where data sets on the order of $O(10^8)$ pixels can be analyzed in a timely fashion. The foregoing systems and methods are applicable to many industries, including subterranean water and hydrocarbon reservoir analysis, mining, tissue analysis, and structural analysis of materials. The clustering methods disclosed above have even wider application including statistical data analysis and information mining in small and large data sets from all fields of endeavor including, in particular, genetics and other medical sciences.

What is claimed is:

1. A method that comprises:
   acquiring two-dimensional (2D) or three-dimensional (3D) digital images of a rock sample;
   iteratively analyzing property measurements collected throughout the digital images using different subsample sizes to identify a property distribution convergence as a function of subsample size, wherein iteratively analyzing property measurements comprises representing property measurements as a set of data points and grouping the set of data points into clusters by computing a parameterized function representing a log-likelihood and a single property measurement using at least one Gaussian component, such that the clusters are a best representation of the set of data points; and
   selecting a smallest subsample size associated with the property distribution convergence as a representative elementary area or volume for the rock sample.

2. The method of claim 1, wherein computing the parameterized function involves representing a single property measurement using at least two Gaussian components.

3. The method of claim 1, wherein computing the parameterized function involves representing multiple property measurements using at least one Gaussian component for each of the multiple property measurements.

4. The method of claim 1, further comprising assigning a property distribution index value to each of the data points in response to the identified property distribution convergence.

5. The method of claim 4, further comprising spatially assigning a property distribution index value to subsamples in the 2D or 3D digital images and using the distribution index values for subsequent analysis of the rock sample.

6. The method of claim 1, further comprising maximizing the parameterized function by splitting or merging the at least one Gaussian component.

7. The method of claim 6, further comprising updating merge criteria in response to a determination that property distribution convergence to a threshold tolerance is not reached.

8. The method of claim 6, further comprising applying a merge criteria based on a Sturges formulation.

9. The method of claim 1, further comprising comparing Gaussian components corresponding to different subsample sizes to identify the property distribution convergence as a function of subsample size.

10. A system that comprises:
    a memory having software; and
    one or more processors coupled to the memory to execute the software, the software causing the one or more processors to:
    acquire two-dimensional (2D) or three-dimensional (3D) digital images of a rock sample;
    iteratively analyze property measurements collected throughout the digital images using different subsample sizes to identify property distribution convergence as a function of subsample size;
    represent property measurements as a set of data points by grouping the set of data points into clusters and computing a parameterized function representing a log-likelihood such that the clusters are a best representation of the set of data points, wherein the parameterized function is computed by representing a single property measurement using at least one Gaussian component; and
    select a smallest subsample size associated with the property distribution convergence as a representative elementary area or volume for the rock sample.

11. The system of claim 10, wherein the software further causes the one or more processors to represent a single property measurement using at least two Gaussian components.

12. The system of claim 10, wherein the software further causes the one or more processors to represent multiple property measurements using at least one Gaussian component for each of the multiple property measurements.

13. The system of claim 10, wherein the software further causes the one or more processors to assign a property distribution index value to each of the data points in response to the identified property distribution convergence.

14. The system of claim 10, wherein the software further causes the one or more processors to spatially assign a property distribution index value to subsamples in the 2D or 3D digital images and to use the distribution index values for subsequent analysis of the rock sample.

15. The system of claim 10, wherein the software further causes the one or more processors to compare Gaussian components corresponding to different subsample sizes to identify property distribution convergence as a function of subsample size.

16. The system of claim 10, wherein the software further causes the one or more processors to maximize the parameterized function by splitting or merging the at least one Gaussian component.

17. The system of claim 16, wherein the software further causes the one or more processors to update merge criteria in response to a determination that property distribution convergence is not reached.

18. The system of claim 16, wherein the software further causes the one or more processors to apply a merge criteria based on a Sturges formulation.

* * * * *